US011307103B2

(12) United States Patent
Betz et al.

(10) Patent No.: US 11,307,103 B2
(45) Date of Patent: Apr. 19, 2022

(54) METHOD AND DEVICE FOR DETERMINING A MECHANICAL LOAD

(71) Applicant: Ottobock SE & Co. KGaA, Duderstadt (DE)

(72) Inventors: Sebastian Betz, Göttingen (DE); André Mueller, Duderstadt (DE)

(73) Assignee: Ottobock SE & Co. KGaA, Duderstadt (DE)

( * ) Notice: Subject to any disclaimer, the term of this patent is extended or adjusted under 35 U.S.C. 154(b) by 168 days.

(21) Appl. No.: 16/615,790

(22) PCT Filed: May 18, 2018

(86) PCT No.: PCT/EP2018/063190
§ 371 (c)(1),
(2) Date: Nov. 21, 2019

(87) PCT Pub. No.: WO2011/215365
PCT Pub. Date: Nov. 29, 2018

(65) Prior Publication Data
US 2020/0182713 A1 Jun. 11, 2020

(30) Foreign Application Priority Data
May 22, 2017 (DE) ...................... 10 2017 111 099.2

(51) Int. Cl.
*G01L 5/00* (2006.01)
*G01L 1/16* (2006.01)
(Continued)

(52) U.S. Cl.
CPC .................. *G01L 1/16* (2013.01); *A61F 2/76* (2013.01); *A61F 5/01* (2013.01); *G01L 5/00* (2013.01);
(Continued)

(58) Field of Classification Search
CPC . A61B 5/4528; G01L 1/16; G01L 5/00; A61F 2/76; A61F 5/01; A61F 2/70;
(Continued)

(56) References Cited

U.S. PATENT DOCUMENTS 8,291,779 B2 * 10/2012 Helmer .................. G01D 5/165
73/865.4
9,310,801 B2 * 4/2016 Frydendal .......... G05B 23/0221
(Continued)

FOREIGN PATENT DOCUMENTS

DE 10250670 A1 5/2003
DE 102015009220 A1 1/2017
(Continued)

*Primary Examiner* — Octavia Hollington
(74) *Attorney, Agent, or Firm* — Holland & Hart LLP (57) ABSTRACT

A method for determining a mechanical load to which a component was exposed. The component comprises at least one sensor that is arranged in a force flow of the mechanical load and that emits a measurement signal in the event of a mechanical load. The method comprises providing an increase function, which establishes a relationship between the measurement signal and the mechanical load for an increasing load, providing a decrease function, which establishes a relationship between the measurement signal and the mechanical load for a decreasing load, identifying reversal points at which a change in the measurement signal changes a sign, saving the measurement value and the corresponding increase functional value or decrease functional value at the reversal point, providing a new increase function or a new decrease function by displacing and compressing the increase function or the decrease function, wherein the compression is executed with regards to both the measurement signal and the mechanical load, and determining the mechanical load at least also using the saved values.

22 Claims, 6 Drawing Sheets

(51) Int. Cl.
   *A61F 2/76*   (2006.01)
   *A61F 5/01*   (2006.01)
   A61F 2/70    (2006.01)
   A61F 2/48    (2006.01)

(52) U.S. Cl.
   CPC ............... *A61F 2/488* (2021.08); *A61F 2/70* (2013.01); *A61F 2002/7635* (2013.01); *A61F 2005/0188* (2013.01)

(58) Field of Classification Search
   CPC ........ A61F 2002/488; A61F 2002/7635; A61F 2005/0188
   USPC .................................................. 73/862.625
   See application file for complete search history.

(56) References Cited

U.S. PATENT DOCUMENTS

2010/0191153 A1    7/2010  Sanders et al.
2016/0153828 A1*   6/2016  Kneubuhl ............ G01G 19/022
                                                 73/862.625

FOREIGN PATENT DOCUMENTS

| EP | 0457134 A2 | 11/1991 |
| EP | 3040168 A1 | 7/2016 |
| WO | 2011069495 A1 | 6/2011 |

* cited by examiner

METHOD AND DEVICE FOR DETERMINING A MECHANICAL LOAD

CROSS REFERENCE TO RELATED APPLICATIONS

This application is a U.S. National Entry and claims priority to PCT International Patent Application No. PCT/EP2018/063190, filed May 18, 2018, and entitled "METHOD AND DEVICE FOR DETERMINING A MECHANICAL LOAD", which claims priority to Patent Application No. DE 10 2017 111 099.2 filed May 22, 2017, the entire disclosures of which are incorporated herein by this reference.

TECHNICAL FIELD

The invention relates to a method for determining a mechanical load to which a component was exposed, wherein the component comprises at least one sensor that is arranged in a force flow of the mechanical load and that emits a measurement signal in the event of a mechanical load.

BACKGROUND

This type of method and a corresponding device is described, for instance, in WO 2011/069495 A1. Components which are exposed to a mechanical load, especially a recurring mechanical load, have a limited operating life. Material fatigue occurs, such that the component must be replaced after a certain operating life. In the case of structures that are subjected to considerable mechanical loads, such as bridges, analyses can be carried out from which a degree of wear and thereby a remaining operating life can be derived, wherein said operating life refers to the period during which the component can be safely operated. This is not possible with smaller and cheaper components, such as those used in orthopedic technology. In particular, orthoses or prosthesis that are used, for example, in a healing process are, however, only used by a patient for a certain period of time, for instance during a recovery phase. To be able to determine whether, at a later point in time, such an orthosis or prosthesis can be provided to a second patient, it must be ensured that the material fatigue caused by the first patient's use is not yet so advanced that it poses a health risk to the second or any further patient. To this end, it is common to use load sensors in the force flow of a component, especially of an orthopedic aid, wherein the sensor may be, for instance, a piezoelectric element.

If the component is now exposed to a mechanical load, said load acts on the at least one sensor, since it is arranged in the force flow of the load. It then emits a measurement signal which, in the event of a piezoelectric element, may be an electrical current, for example. WO 2011/069495 A1 describes how to store and accumulate this current in a different way and thereby obtain a measure of how much load acted cumulatively on the sensor and therefore also on the component. However, experience shows that this method only allows for a highly imprecise and often insufficient indication of a remaining operating life.

SUMMARY

The invention therefore aims to further develop a method of the type described above in such a way that the load to which a component was exposed can be determined easily and as precisely as possible, The invention solves the problem by way of a method of the type described above that comprises the following steps:

a) providing an increase function, which establishes a relationship between the measurement signal and the mechanical load for an increasing load, b) providing a decrease function, which establishes a relationship between the measurement signal and the mechanical load for a decreasing load, c) identifying reversal points at which a change in the measurement signal changes a sign, d) saving the measurement value and the corresponding increase functional value or decrease functional value at the reversal point, e) providing a new increase function or a new decrease function by displacing and compressing the increase function or the decrease function, wherein the compression is executed with regards to both the measurement signal and the mechanical load, and f) determining the mechanical load at least also using the saved values.

The invention is based on the knowledge that mechanical load sensors, such as piezoelectric elements, deliver results that are affected by hysteresis. This means that, for example, a piezoelectric element generates an electrical current and therefore also a charge displacement when a load is present, wherein, however, there is no unambiguous relationship between the force acting on the element and the displaced charge. In the event of an increasing force, a piezoelectric element delivers different measurement signals than in the event of a decreasing force, although on a point-by-point basis, the same forces are acting on the piezoelectric element. This is the case with a number of mechanical sensors and it means that simply knowing a measurement signal, such as the volume of a displaced charge of a piezoelectric element, is not sufficient to make explicit conclusions concerning an acting force or load. The result of this is that, with methods known from the prior art, in which only the volume of the displaced charge, i.e. the electrical current, is cumulatively stored, it is not possible to draw any conclusions concerning the mechanical loads that acted on the component.

The invention takes this information into account. First of all, an increase function and a decrease function are provided. Here, the increase function establishes the relationship between the measurement signal, such as the displaced charge or the electrical current of a piezoelectric element, and the mechanical load, i.e. such as the acting compressive force, if the load increases. The decrease function establishes the relationship between these two variables in the event of a decreasing load.

Here, the increase function and the decrease function are preferably adjusted to the respective sensor in use and its hysteresis function, such that they reflect the actual course of the measurement signal depending on the load that occurs for an increasing load and a decreasing load as correctly and accurately as possible. This may be achieved, for example, by fitting measurement values by a function. This ensures that both functions can be used effectively in the fitted area. Furthermore, the two functions potentially do not reflect the actual behavior of the sensor with the same degree of accuracy, for instance in the event of greater loads. This does not depend on how the functions have been identified and provided. They have a scope of application or validity in which they can be used effectively and a range beyond in which the accuracy with which the functions reflect the actual relationship reduces or is unknown. The range of the measurement signals in which the respective function effectively and correctly reflects the actual relationship is hereinafter referred to as the functional range. The corresponding range of the mechanical load is referred to as the value range.

Over the course of the mechanical load to which the component is exposed, an increase or a decrease in the mechanical load, for instance of an exerted pressure, may occur. The points at which the change in the measurement signal—and therefore also in the load—changes the sign are referred to as reversal points and are identified in step c) of the method. Consequently, at a reversal point the load changes from an increasing load to a decreasing load or from a decreasing load to an increasing load. It therefore refers to the points at which the relevant function has to be changed for the respective relationship between the measurement signal and the mechanical load. Whereas, in the event of an increasing measurement signal and therefore an increasing load, the increase function establishes the relationship between measurement signal and load, the decrease function relates to a decreasing measurement signal and therefore a decreasing load. Consequently, the function, by way of which the relationship between the measurement signal of the at least one sensor and the mechanical load is correctly reflected, changes at a reversal point.

Such reversal points are identified and stored by storing the respective measurement value, which is emitted by the sensor at the reversal point, and the respective increase function value or decrease function value at the reversal point. These can then be used to subsequently determine the mechanical load to which the component was exposed.

A new increase function or a new decrease function is calculated for each reversal point. Here, an increase function is calculated if the reversal point is a local minimum, and a decrease function is calculated if the reversal point is a local maximum. This is achieved by displacing the existing increase or decrease function and compressing it both in relation to the measurement signal, i.e. in the x direction, and in relation to the mechanical load, i.e. in the y direction. Here, the displacement and compression occur in such a way that the functional range of the function to be compressed fits in the range between the measurement value of the identified reversal point and the measurement value of the preceding reversal point, and the value range fits in the range between the two corresponding functional values.

Preferably, the increase functional value at the reversal point is stored in step d) of the method if the reversal point is a local load maximum. This means that at the reversal point, an increasing load changes into a decreasing load. In this case, the functional value of the increase function should be saved. Conversely, the decrease function is preferably saved if the reversal point is a local load minimum. In this case, at the reversal point, the load changes from a decreasing load into an increasing load. In this case, the functional value of the decrease function should be saved.

In a preferred embodiment of the method, the identification of a reversal point is followed by the provision of a new increase function or a new decrease function. This may be done either before or after saving the respective measurement values or the functional values. If the reversal point is a local load maximum, the load at this point consequently changes from an increasing load into a decreasing load; a new decrease function is provided, since it correctly reflects the relationship between the measurement signal and the mechanical load in the subsequent decreasing load. However, if the reversal point is a local load minimum, at which the load consequently changes from a decreasing load into an increasing load, a new increase function is provided, since it correctly reflects the relationship between measurement signal and load in the subsequent increasing load.

Preferably, the new increase function or the new decrease function is calculated from the current increase function or the current decrease function and the reversal point and the previous two reversal points. If, for example, a new increase function is required, in order to provide this new increase function, the current increase function is needed along with the reversal point that has just been reached and the two previous reversal points, between which the functional range of the current increase function extended. Here, both the measurement signal of the reversal point, i.e. the measurement value that the sensor emitted at this point, and the respective increase function value at this point, i.e. the measured mechanical load, are used. In the same way, if a new decrease function is required, the current decrease function and the reversal point that has just been reached are needed, as well as the two previous reversal points, between which the functional range of the current decrease function extended.

Alternatively, the new increase or decrease function can be calculated from an earlier increase or decrease function, such as the original increase or decrease function, and the reversal points, between which the functional range of this function extended, and all reversal points saved since.

Preferably, prior to the first load, a base increase function and a base decrease function are provided and, in particular, identified using measurement data from at least one sensor. These can be recorded, for instance, experimentally and subsequently fitted. Here, the base increase function and the base decrease function are defined in a range between a minimal load and a maximum load. The maximum load should be selected in such a way that during operation of the component, i.e. when actual loads occur, it is not exceeded. The base increase function and the base decrease function therefore have a functional range that comprises the anticipated loads between the minimum load and the maximum load. Both functions also feature a corresponding value range. Each of the two functions provides a clear mapping between a load that acts on the component, i.e. a functional value of the increase function or the decrease function, and an emitted measurement signal or measurement value of the sensor, i.e. for example an electrical current or an electrical charge, to which the respective load can be unambiguously allocated. If a new increase function or a new decrease function is now to be calculated from the base increase function or the base decrease function, three reversal points are required, amongst other factors. These comprise the reversal point that has just been reached, which renders necessary the provision of a new increase function or a new decrease function, and the two previous reversal points, between which the functional rage of the current function extends. At each of these reversal points, the measurement value of the sensor and the corresponding load were saved, said load having been calculated using the respective current increase function or current decrease function. The base increase function is now compressed in both the value range and the functional range in such a way that it goes from the reversal point that has just been reached to the previous reversal point.

This is true for both a base increase function and a base decrease function. In general, it has been proven practical if this method is used to determine a new increase function or a new decrease function from a current increase function or a current decrease function.

Preferably, values that are saved in step d) of the method once a reversal point has been reached are deleted if this reversal point is reached again or passed. This reduces the memory required for storing the various values.

The invention also solves the problem by way of a component, especially a part of an orthopedic device, that features at least one sensor and an electronic data processing device with at least one processor, said data processing device being configured to conduct a method according to the type described here.

This preferably involves the running of a program for the processing of electronic data and it is conducted by the least one processor.

It is preferable if the at least one sensor has at least one piezoelectric element, preferably a piezoceramic element. It has been proven especially practical if the at least one sensor comprises several, preferably six, piezoelectric elements. These may be arranged, for instance, about a central symmetrical axis of the component. Here, an equidistant arrangement has been proven to be advantageous. This enables not only the calculation and totalling of values of loads, but also, for example, the distinctive treatment and separation of loads acting in different directions.

The component preferably has at least one memory, in which the values from step d) of the method are saved.

Certain measurement methods and measurement relationships of sensors may contain an inherent measurement error that accumulates over time. This is especially true of integrative measurement methods, such as the measurement of charge in piezoelectric sensors, which occurs via the integration of the respective electrical current generated in the piezoelectric element. This is especially common if a zero point of the measurement was not calibrated with sufficient accuracy or it was calibrated incorrectly, or if said zero point moves during the measurement. In the case of a piezoelectric force or load sensor, this means that the sensor is not in the same condition following the completion of a load cycle as it was before. Within the scope of a diagram, in which the exerted force is plotted over the emitted measurement signal, this means that the load cycle does not form a closed trajectory; rather, it features an opening. Conversely, an erroneous calibration of the sensor only means that the value of a force that is acting at a certain point in time, wherein said value is extracted from the measurement data of the sensor and should be detected by the piezoelectric sensor, is perceived as being too large, for example. However, given that, with piezoelectric elements, the measurement value is generated by the temporal integration of a physical variable, i.e. the total charge, for instance, by way of the integration of the generated electrical current, such an erroneous calibration or displacement of the zero point also leads to a measurement error, in the same way as a not quite closed cyclical trajectory of the cyclical load, wherein said measurement error is integrated over time and thus increases in significance until it is potentially of the same size as the actual measurement signal.

In order to prevent this from happening, it is beneficial to compare the measurement signal with known reference points, so as to be able to eliminate such integrated measurement errors. If such a reference point is known, it can be used to nullify accumulated measurement deviations caused by signal drift or incorrect calibration. In the field of prosthetics, such a point exists for the comparison of the signal, for example during the swing phase of a gait cycle, given that, at this point in time, the piezoelectric force or load sensors are at least almost, however preferably completely, free from external loads. To this end, it is advantageous if the sensors do not have any pre-loads, which are otherwise present in the swing phase, such that in this case, this point in time is not suitable—or only to a limited extent—to act as a reference point.

In an especially preferred embodiment, the reference point for the purpose of comparison is preferably identical to the starting point of the base increase function. This is precisely the case if there is no pre-load force acting on the sensors.

The sensor is preferably adjusted by allocating, under pre-determined conditions, a corresponding measurement value to a known load and providing a previously known increase function and a previously known decrease function. In particular, if the method is used with an orthosis or prosthesis, the pre-determined conditions may be a certain situation of movement, such as a swing phase in a gait cycle. It is practical to select the pre-determined conditions in such a way that there is no load acting on the component at the moment when the sensor is adjusted. In this case, it is possible that, in accordance with the known load value "0", a value "0" is also allocated to the measurement signal. In this case, the base increase function and the base decrease function are preferably provided as increase function and decrease function, respectively. In this case, the calculation of further increase and decrease functions upon reaching various reversal points occurs in the same way as the original calculation at the start of the method.

Here, it is preferable if reversal points that were saved prior to the adjustment of the sensor are not used in order to calculate a new increase function or a new decrease function. These are affected by the measurement error that is eliminated by the adjustment and would therefore render the result incorrect.

Preferably, for at least one reversal point, but preferably several, especially preferably all reversal points, a difference between the functional value to be saved and the functional value saved for the previous reversal point is also saved, as well as a mean value between these two functional values. This method is based on the knowledge that, if the difference between a local maximum and a local minimum of the load is the same, the effect on the respective component also depends on the absolute value of the load. Given that, in this beneficial case, the mean value between the two functional values is determined and saved, it can be tracked retrospectively, such that load cycles that occur in the event of a large load can be weighted differently in retrospect and thereby have a greater influence on the final result.

The method is preferably applied for an orthosis or prosthesis, or for a component of an orthosis or a component of a prosthesis. The component described here is preferably an orthosis or a prothesis, or a component of an orthosis or a component of a prosthesis.

In the field of prosthetics and orthoses, especially with leg prosthetics and orthoses that are subjected to considerable loads when walking, a cyclical continuous load occurs not only on the prosthesis or orthosis, but also particularly on the piezoelectric sensors. It has been demonstrated that, in the event of a cyclical continuous load, a depolarization of piezoelectric elements may occur. This may be caused, for instance, by folding processes in the domain structure of the piezoceramic material. This means that, from load cycle to load cycle, a smaller charge is generated and the output signal decreases relative to the first load. A cyclical continuous load that occurs at a constant maximum load achieved in each cycle thus leads to a cyclical decrease in the respective sensor signal and therefore to a permanent distortion of measurement values. The maximum value of the base increase function and the base decrease function decreases correspondingly from load cycle to load cycle.

Here, the depolarization itself follows a logarithmic function, which can also be mathematically fitted and thus compensated. The correction is conducted with the aid of a correction factor, which is multiplied by the base increase function and the base decrease function. It can be calculated with the aid of the logarithmic function that was previously fitted using measurement values.

In the following, an example of an embodiment of the present invention will be explained in more detail by way of the attached figures: They show:

DETAILED DESCRIPTION

Figure 1:
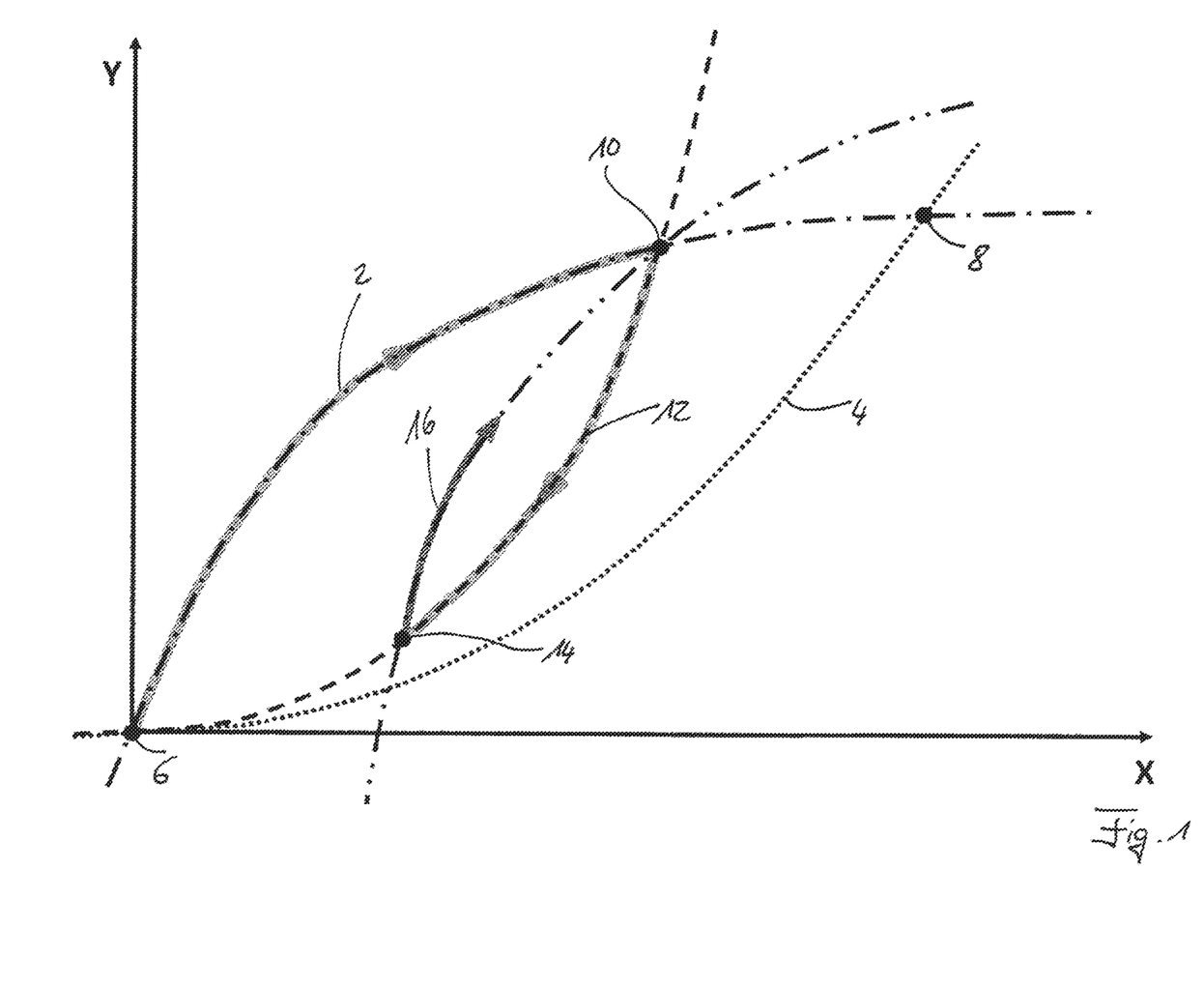
FIG. 1—a exemplary schematic load curve,
FIGS. 2 to 4—the schematic depiction of different steps of the method,
FIG. 5—the effect of integrated measurement errors, and
FIG. 6—the effect of depolarization.

FIG. 1 shows a diagram in which a measurement value, such as an electrical charge, generated by a piezoelectric sensor is plotted on the x axis and, as a function thereof, an applied force is plotted on the y axis. First of all, for a method according to the present invention, an increase function 2 and a decrease function 4 are provided. Their functional range extends between a zero point 6 and a maximum load point 8 if the functions refer to a base increase function and a base decrease function.

In the first section of the load curve depicted in FIG. 1, the force acting on the sensor is increased, such that the measurement value moves along the increase function 2 to the first local maximum point 10. This is a first reversal point at which the applied load does not continue to increase over time; rather, it decreases. The corresponding measurement value and the corresponding increase functional value at this reversal point are saved.

A new decrease function 12 is now determined by compressing and displacing the current decrease function 4, whose functional range extends between the zero point 6 and the maximum load point 8, in the x and y direction in such a way that it extends between the first local maximum point 10, i.e. the reversal point currently reached, and the zero point 6. In the event of a decreasing load, the corresponding measurement value now moves along this new decrease function. This continues until the force reaches a first local minimum point 14, which is once again a reversal point. Here, the measurement value and the corresponding decrease function value are also saved. It is now necessary to determine a new increase function 16. along which the measurement moves in the event of an increasing load. To achieve this, the current increase function 2, whose functional range extends between the zero point 6 and the maximum load point 8, is compressed and displaced in the x and y direction in such a way that it extends from the first local minimum point 14 to the first local maximum point 10. In the event of an increasing load Y, the measurement value now moves along this new increase function. If the load is further increased beyond the first local maximum point 10, the measurement value continues to follow the current increase function 2.

Figure 2:
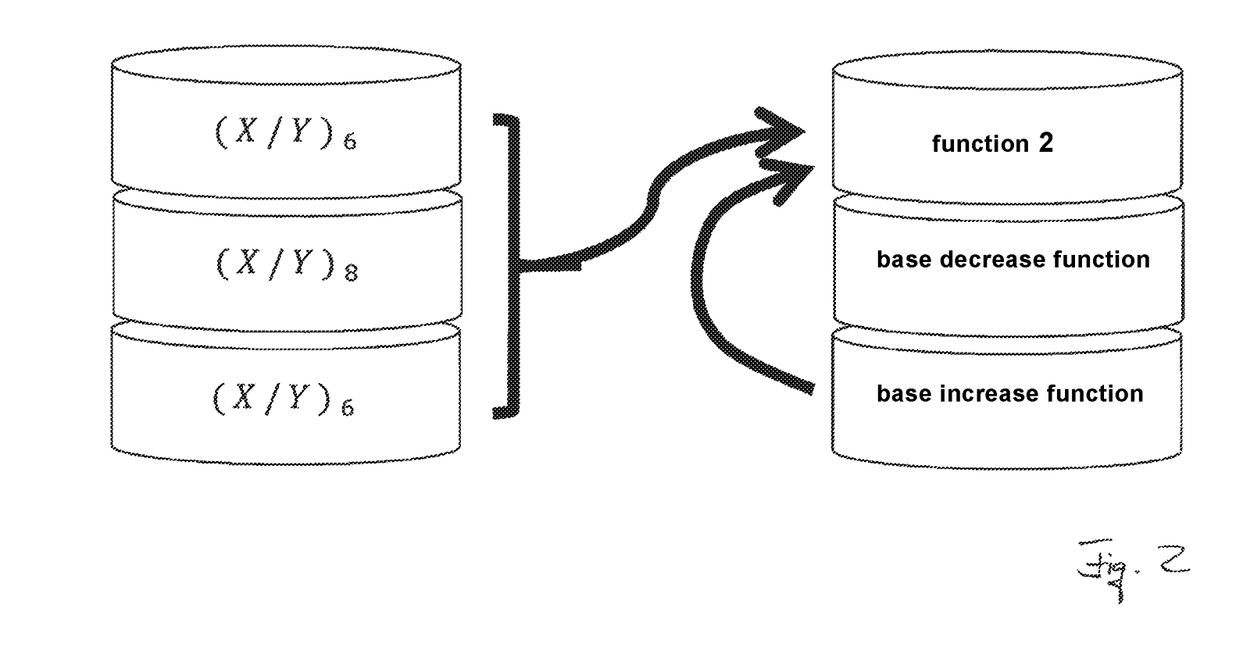
Figure 3:
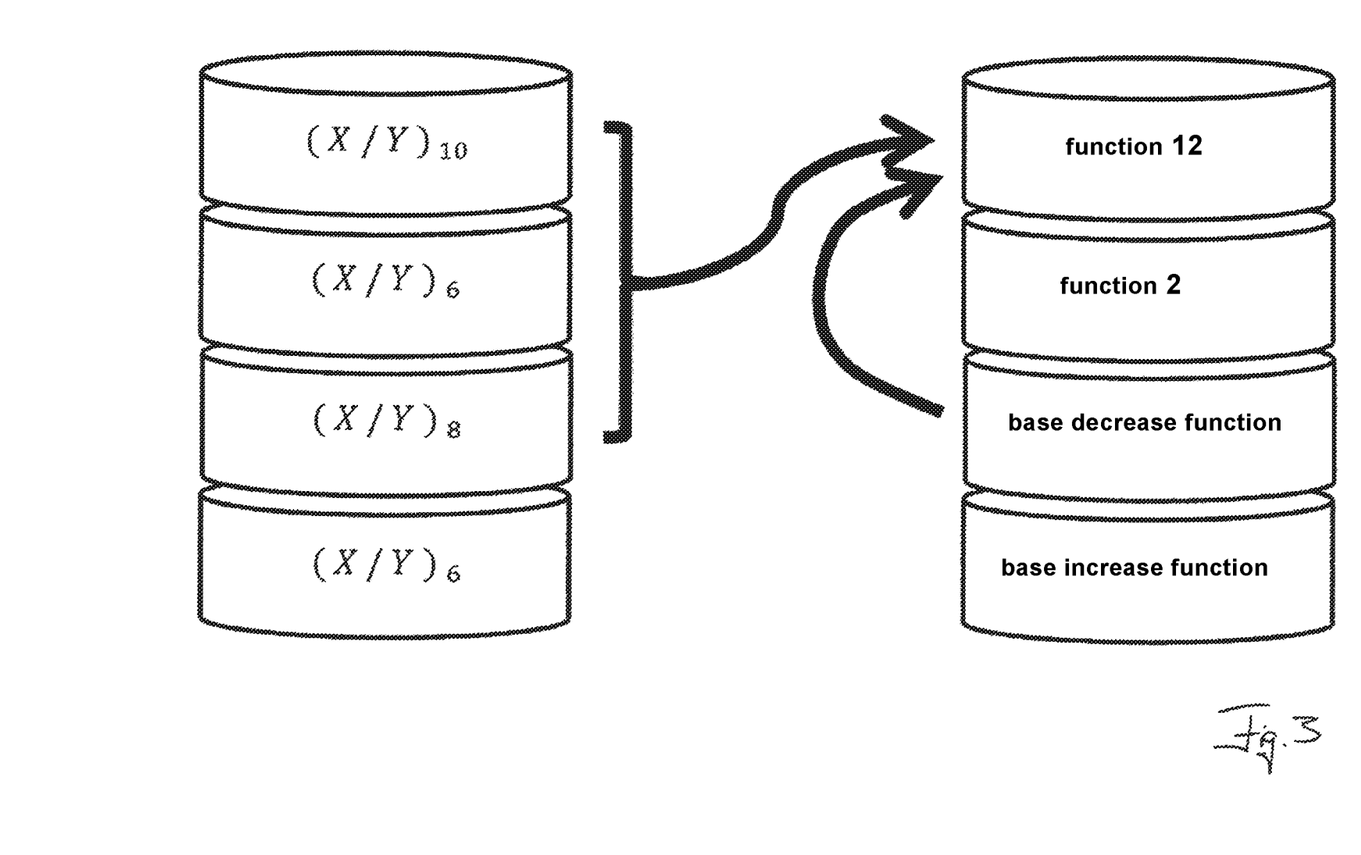
Figure 4:
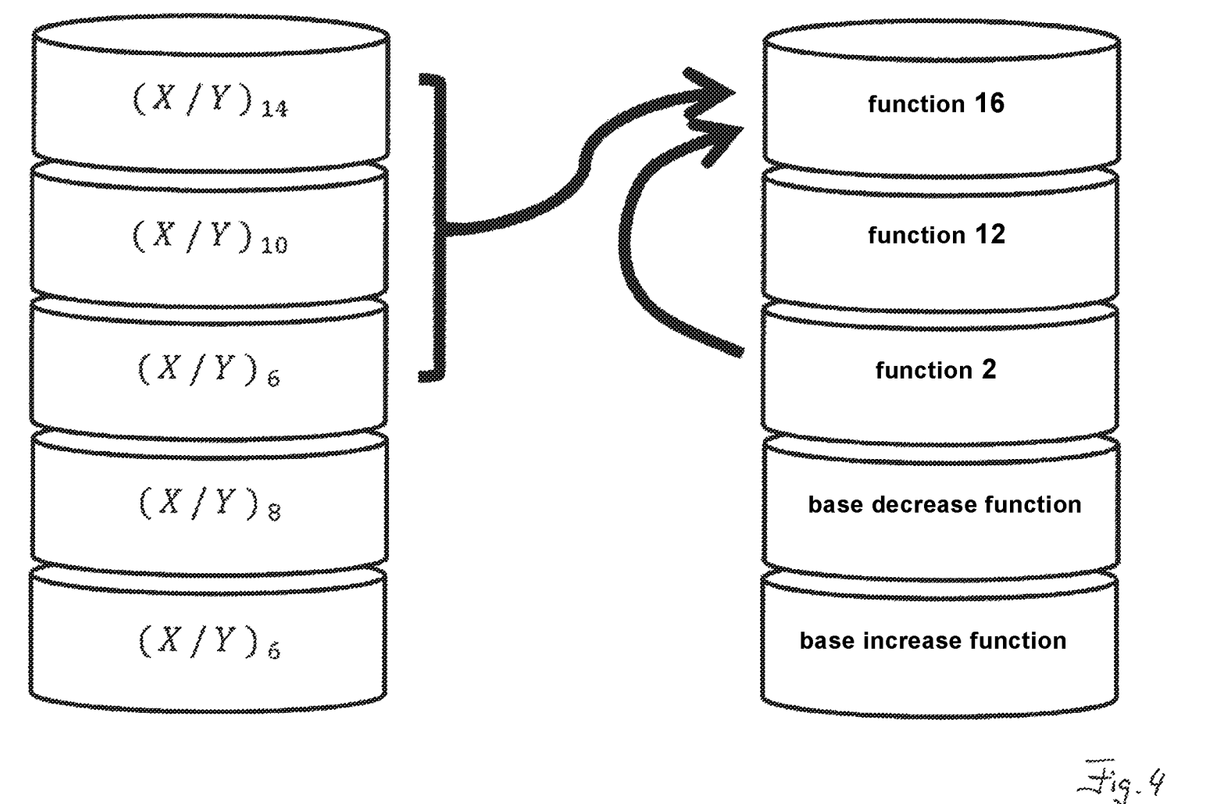

FIGS. 2 to 4 schematically depict the different saved values and data at the steps in the process described so far, which are necessary for a course according to FIG. 1. The right-hand stack in FIG. 2 shows that the base increase function and the base decrease function must first of all be saved. Their functional range extends between the zero point 6 and the maximum load point 8, as shown in FIG. 1. Therefore, points, i.e. measurement values X and corresponding functional values, i.e. loads Y, are stored in the memory stack depicted on the left; these points are depicted in the form of X/Y coordinate pairs. The index designates the reference that identifies the respective point in FIG. 1.

FIG. 2 shows the situation that occurs at the beginning, at the zero point 6. It refers to a minimum, meaning that a current increase function must first of all be defined. In FIG. 1, this is indicated by the reference 2 and is therefore referred to using the term "function 2" in FIG. 2. It is determined using the previous increase function, i.e. in this case the base increase function, the two points between which its functional range extends, and the current minimum point, which in this case is also the zero point 6. Function 2 thus corresponds to the base increase function, so that this step in the method could also, in principle, be omitted. However, it does serve to clarify the method.

FIG. 3 schematically depicts what happens once the local maximum point 10 has been reached. This refers to a local maximum, such that a new decrease function must be provided, which is indicated by the reference 12 in FIG. 1 and is therefore referred to using the term "function 12" in FIG. 3. It is determined from the current decrease function, which is the base decrease function. The points between which the functional range of this base decrease function is situated are also required. In the example of an embodiment shown, these are the zero point 6 and the maximum load point 8, such that their coordinates, in the form of X/Y pairs, are used with the corresponding index, which corresponds to the references in FIG. 1. In addition, the local minimum point 10 that has just been reached is also used, wherein said point is also placed in the left-hand memory stack in FIG. 3. Here, the X/Y pair is also used with the reference 10. These values and the base decrease function are used to determine the function 12. Here, the base decrease function is compressed and displaced in the x and y direction in such a way that it now extends between the local maximum point 10 and the zero point 6.

This function 12 is used until the measurement value X, i.e. the measurement value caused by a sensor, such as a piezoelectric element, decreases or the measurement value of a value pair in the left-hand stack is reached. The associated functional value Y, which corresponds to, for instance, a force, a torque or a load, therefore decreases. This occurs until the local minimum point 14 is reached in FIG. 1. The method provides for the determination of a new increase function in this case. However, the local minimum point 14 and its coordinate pair X,Y with the index 14 must first be stored, as depicted in the left-hand memory stack in FIG. 4. To determine the new increase function, which is given the reference 16 in FIG. 1 and is therefore indicated by the term "function 16" in FIG. 4, the function 2 must now be compressed and displaced such that it extends between the local minimum point 14 and the local maximum point 10. Both values must therefore be included in the calculation. In addition, the zero point 6 and its value pair X/Y is used, since the functional range of function 2 extends between said point and the local maximum point 10. If, by following the function 16, the local maximum point 10 is reached once again, the two top-most entries in each stack are deleted and, from that point onwards, function 2 is followed. This may occur in any closed loop.

This renders it possible to model and later correspondingly evaluate highly complicated load curves.

Figure 5:
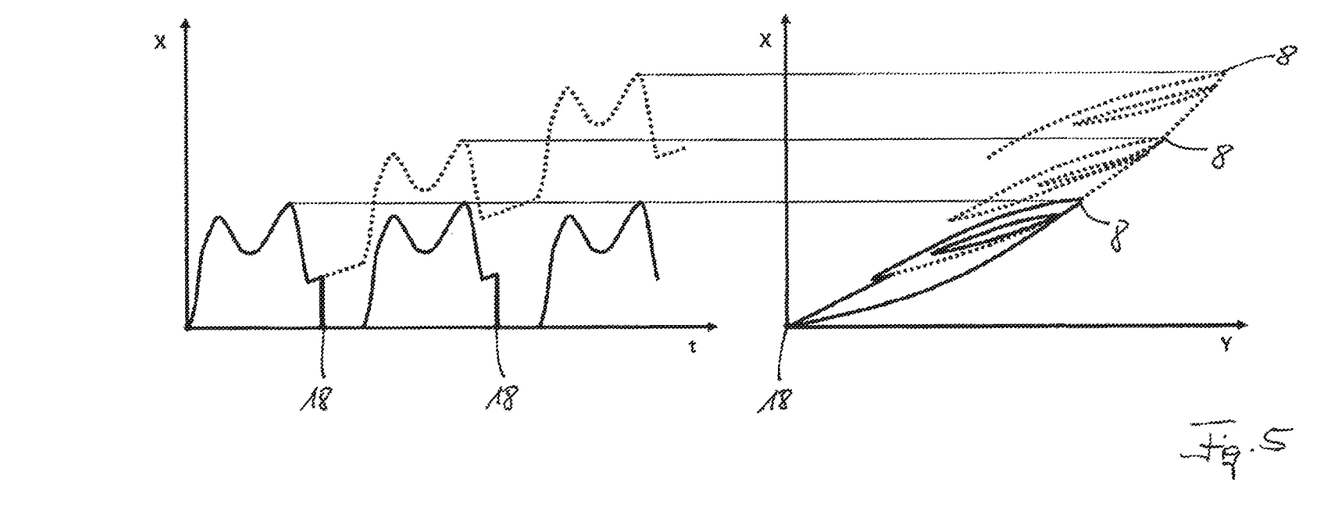

The right-hand diagram in FIG. 5 depicts another measurement value-load diagram, wherein it must be noted that, in comparison to FIG. 1, the axes have been switched. A cyclical load, consisting of three cycles—depicted by a dashed line—is clearly visible. Due to an integrated measurement error, the entire measurement value sequence moves with every cycle, as does, in particular, the respective maximum load point 8 at higher measurement values and therefore, supposedly, higher loads. On the left of FIG. 5, the translation of the data is transferred to a diagram, in which the measured value is once again depicted on the x axis as a function of time. The dashed line shows the measurement value at which the measurement value was integrated. It is clear that the presumed peak load increases with every cycle. The solid line depicts the progression of an adjusted measurement value. This value can be reached by comparing the measurement signal with a known reference point 18 between every load cycle. This reference point 18 may lie, for example, in the swing phase of a gait cycle, during which the respective piezoelectric sensor is load-free. Since this is known, the measurement signal identified at this point can be nullified, so that signal drift or any other integrated measurement errors can be eliminated.

Figure 6:
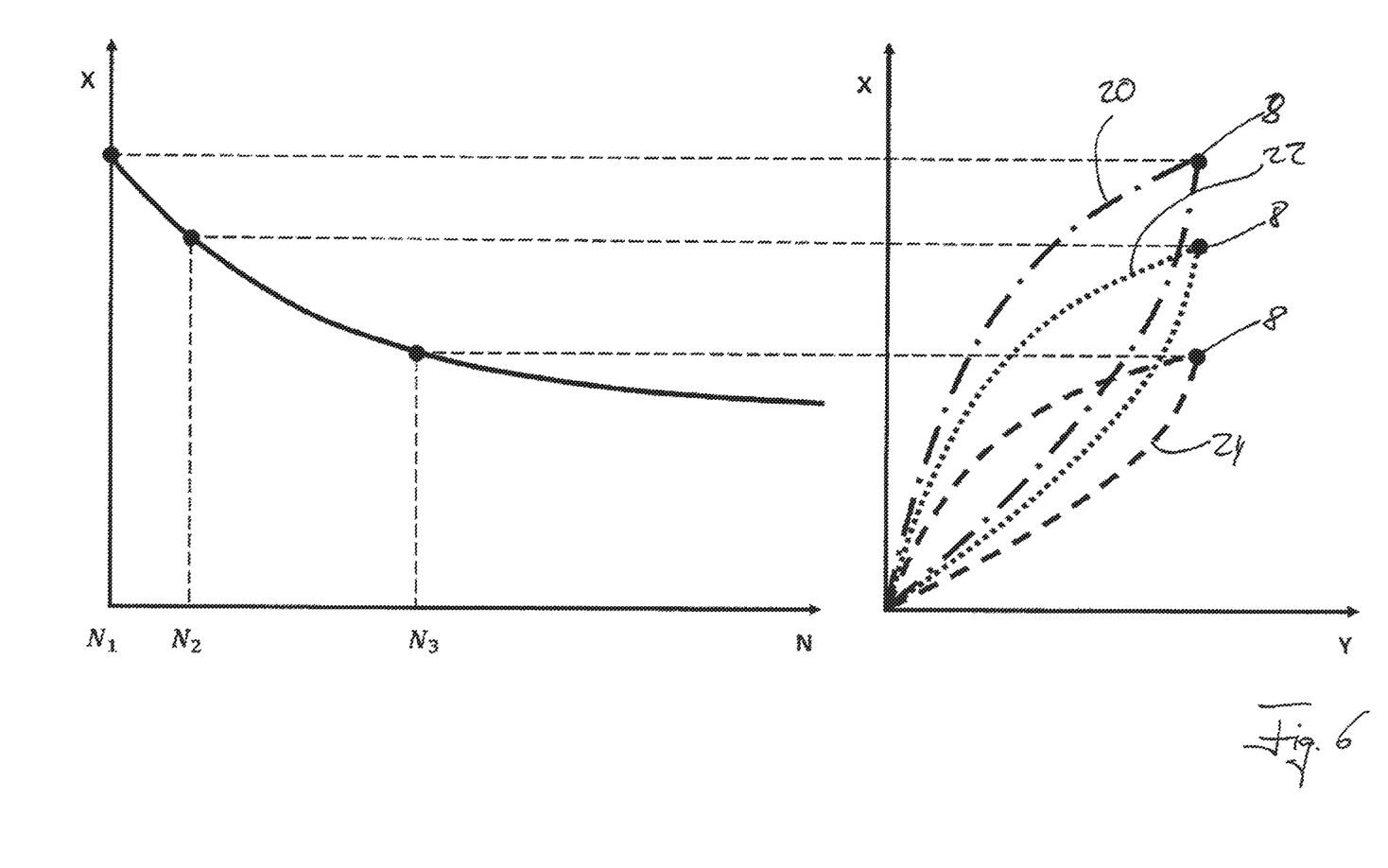

As in FIG. 1, the right-hand example in FIG. 6 features a depicting in which a measurement value is plotted on the x axis over the applied load. In comparison to FIG. 1, the axes have also been switched. Here, the loads are cyclical, said loads being depicted by way of three separate cycles with differently dashed lines. The cycle depicted with a dash-dot line 20 occurs considerably earlier than the cycle depicted with the line 22, which in turn occurs considerably earlier than the cycle depicted with a dashed line 24. It is clear to see that the maximum load point 8 decreases in every cycle, which can be attributed to the known depolarization effect during a cyclical continuous load. To the left, the respective presumed load point is plotted as a function of the respective cycle number N. There is a clear logarithmic course. If this course is known, it is possible to compensate the measured values by way of a stored correction function.

We claim:

1. A method for determining a mechanical load to which a component was exposed, wherein the component comprises at least one sensor that is arranged in a force flow of the mechanical load and that emits a measurement signal in the event of a mechanical load, wherein the method comprises:
   providing an increase function, which establishes a relationship between the measurement signal and the mechanical load for an increasing load;
   providing a decrease function, which establishes a relationship between the measurement signal and the mechanical load for a decreasing load;
   identifying reversal points at which a change in the measurement signal changes a sign, wherein the reversal points comprise a first local maximum point and a first local minimum point;
   storing the measurement value and a corresponding increase functional value or decrease functional value at the reversal points;
   providing a new increase function or a new decrease function by displacing and compressing the increase function or the decrease function, wherein the compressing is executed with regards to both the measurement signal and the mechanical load, and wherein the increase function is displaced and compressed such that the new increase function extends between the first local maximum point and the first local minimum point; and
   determining the mechanical load at least also using the stored values.

2. The method according to claim 1, wherein the increase functional value is stored if the reversal point is a local load maximum and the decrease functional value is saved if the reversal point is a local load minimum.

3. The method according to claim 1, wherein the new increase function or the new decrease function is calculated from the previous increase function or the current decrease function and the reversal point and the previous two reversal points.

4. The method according to claim 1, wherein a base increase function and a base decease function are provided prior to the first load, and the base values are identified using measurement data from the at least one sensor.

5. The method according to claim 1, wherein the values are stored once a reversal point has been reached and are deleted if the reversal point is reached again or passed.

6. The method according to claim 1, wherein the sensor is adjusted by allocating, under pre-determined conditions, a corresponding measurement value to a known load and providing a previously known increase function and a previously known decrease function.

7. The method according to claim 6, wherein the load and the allocated measurement value are both zero, and the increase function is the base increase function and the decrease function is the base decrease function.

8. The method according to claim 6 wherein the reversal points that were saved prior to the adjustment of the sensor are not used to calculate a new increase function or a new decrease function.

9. The method according to claim 1, wherein at every reversal point, a difference between the functional value to be saved and the functional value saved for the previous reversal point is also saved, as well as a mean value between these two functional values.

10. The method according to claim 1, wherein the component is an orthosis or a prosthesis or a component thereof.

11. A component of an orthopedic device, which includes the component and at least one sensor of claim 1, and an electronic data processing device with at least one processor, which is configured to conduct the method according to claim 1.

12. The component according to claim 11, wherein the at least one sensor has at least one piezoelectric element.

13. The component according to claim 11, wherein the at least one sensor comprises several piezoelectric elements.

14. The component according to claim 11, wherein the component features at least one memory, in which the values are stored.

15. The component according to claim 11, wherein the component is an orthosis or a prosthesis or a component thereof.

16. The method according to claim 1, wherein the decrease function is displaced and compressed such that the new decrease function extends between the first local maximum point and a zero point.

17. A method to determine a mechanical load applied to a component of an orthopedic device, the component comprising at least one sensor that emits a measurement signal in the event of the mechanical load, the method comprising:
   providing an increase function, which establishes a relationship between the measurement signal and the mechanical load for an increasing load;

providing a decrease function, which establishes a relationship between the measurement signal and the mechanical load for a decreasing load;

identifying at least one reversal point at which a sign of the measurement signal changes, wherein the at least one reversal point comprises a first local maximum point and a first local minimum point;

storing the measurement value and a corresponding increase functional value or decrease functional value at the at least one reversal point;

providing a new increase function or a new decrease function by displacing and compressing the increase function or the decrease function, wherein the compressing is executed for both the measurement signal and the mechanical load, and wherein the increase function is displaced and compressed such that the new increase function extends between the first local maximum point and the first local minimum point; and determining the mechanical load using the stored values.

18. The method according to claim 17, wherein the increase functional value is stored if the at least one reversal point is a local load maximum and the decrease functional value is saved if the at least one reversal point is a local load minimum.

19. The method according to claim 17, wherein the new increase function or the new decrease function is calculated from the previous increase function or the current decrease function, and the at least one reversal point and the previous two reversal points.

20. The method according to claim 17, wherein a base increase function and a base decease function are provided prior to the first load, and the base values are identified using measurement data from the at least one sensor.

21. The method according to claim 17, wherein the values are stored once a reversal point has been reached and are deleted if the reversal point is reached again or passed.

22. The method according to claim 17, wherein the decrease function is displaced and compressed such that the new decrease function extends between the first local maximum point and a zero point.

* * * * *